(12) United States Patent
Thrower (10) Patent No.: US 10,328,067 B2
(45) Date of Patent: Jun. 25, 2019

(54) PHARMACEUTICAL ORAL DOSE FORMULATION AND COMPOSITION OF MATTER

(71) Applicant: David W. Thrower, Boca Raton, FL (US)

(72) Inventor: David W. Thrower, Boca Raton, FL (US)

(*) Notice: Subject to any disclaimer, the term of this patent is extended or adjusted under 35 U.S.C. 154(b) by 51 days.

(21) Appl. No.: 15/682,395

(22) Filed: Aug. 21, 2017

(65) Prior Publication Data

US 2018/0055829 A1 Mar. 1, 2018

Related U.S. Application Data

(60) Provisional application No. 62/378,356, filed on Aug. 23, 2016.

(51) Int. Cl.
| | | |
|---|---|---|
| *A61K 31/445* | (2006.01) | |
| *A61K 36/9066* | (2006.01) | |
| *A61K 31/352* | (2006.01) | |
| *A61K 9/107* | (2006.01) | |
| *A61K 9/00* | (2006.01) | |
| *B01D 11/02* | (2006.01) | |
| *A61K 9/14* | (2006.01) | |
| *A61K 9/48* | (2006.01) | |
| *A61K 36/67* | (2006.01) | |
| *A61K 31/12* | (2006.01) | |
| *A61K 31/366* | (2006.01) | |
| *A61K 31/475* | (2006.01) | |

(52) U.S. Cl.
CPC .......... *A61K 31/445* (2013.01); *A61K 9/0053* (2013.01); *A61K 9/1075* (2013.01); *A61K 9/145* (2013.01); *A61K 9/4858* (2013.01); *A61K 31/12* (2013.01); *A61K 31/352* (2013.01); *A61K 31/366* (2013.01); *A61K 31/475* (2013.01); *A61K 36/67* (2013.01); *A61K 36/9066* (2013.01); *B01D 11/0203* (2013.01)

(58) Field of Classification Search
CPC .................................................. A61K 31/445
See application file for complete search history.

(56) References Cited

FOREIGN PATENT DOCUMENTS

WO WO-2005070441 A1 * 8/2005 ......... A61K 36/8962

* cited by examiner

*Primary Examiner* — Benjamin J Packard
(74) *Attorney, Agent, or Firm* — Peter Gutenberg (57) ABSTRACT

An apparatus and method for formulating low solubility, low permeability and/or p-glycoprotein efflux transporter substrate drugs or herbal extracts for increased intestinal absorption. The method utilizes a supercritical fluid, such as carbon dioxide to complex a low solubility, low permeability and/or p-glycoprotein efflux transporter substrate drug or herbal extract, the p-glycoprotein inhibitors quercitin and piperine, with a carbohydrate. The result is a micro-emulsion of the drug or herbal extract which has both higher solubility and permeability than if dosed alone; as well as resistance to p-glycoprotein mediated efflux, once absorbed into the intestinal lumen.

4 Claims, 1 Drawing Sheet

PHARMACEUTICAL ORAL DOSE FORMULATION AND COMPOSITION OF MATTER

FIELD AND BACKGROUND OF THE INVENTION

It has been suggested by many pharmaceutical companies that an oral delivery system is a preferred method of administering therapeutic remedies; it has been estimated that some 85% of all drugs are delivered orally. The ability to deliver a drug orally, allows for increased compliance with the treatment regimen versus an intravenous delivery or even a suppository, which may cause the patient discomfort or subject them to an infection. Other treatments such as inhalation and dermal patches, allow for increased patient compliance versus an intravenous dose, but may require an excess drug product in order to be effective, due to absorption issues and usually requires either expensive equipment or a formulation which is costly to manufacture, test, and administer. Further, oral formulations can be administered without the public noticing while in a public location such as an office or restaurant, where with most other formulations, this may not be the case. The delivery system through which a drug is ingested plays a significant role in the way and the extent to which the compound is absorbed and metabolized. Problems of miscibility and absorption are numerous with such systems. In order to receive the full therapeutic benefit, the drug must be effectively absorbed into the blood stream through the intestine. However, the body possess numerous mechanisms to prevent absorption and expelling a drug back into the intestine before it can reach its site of action. Therein lies the problem, many drug compounds are poorly soluble in an aqueous medium, as found in the stomach, nor will they effectively cross the lumen of the intestine for absorption into the blood stream.

Chief among these mechanisms which prevent absorption through the intestinal wall is that of the p-glycoprotein. The p-glycoprotein is an ATP-powered efflux pump which can transport hundreds of structurally unrelated hydrophobic and amphipathic compounds, including therapeutic drugs, peptides and lipid-like compounds. This polypeptide plays a crucial physiological role in protecting tissues from toxic xenobiotics and endogenous metabolites. This also affects the uptake and distribution of many clinically important drugs. It forms a major component of each of these: the blood-brain barrier, the intestinal lining's defenses against xenobiotics, and the renal tubules mechanisms to accelerate the excretion of many xenobiotics. This transporter restricts the uptake of drugs from the intestine, among other purposes As a guide for predicting the intestinal absorption of drug substances, the U.S. Food and Drug Administration utilizes the Biopharmaceutical Classification System (BCS) to classify drug substances, including small molecule pharmaceuticals and nutraceuticals compounds, based on both permeability and solubility. BCS Class I drug substances are both highly permeable and highly soluble. BCS Class II drug substances are highly permeable, but have low solubility. BCS Class III drug substances are highly soluble, but have low permeability. BCS Class IV drug substances have both low solubility and low permeability.

There are many BCS Class III and IV drug substances which would be effective therapies for a variety of diseases, but for the fact that they poorly absorb or will not absorb through the intestine.

A first example, include the chemotherapeutic agent, vinblastine, which must delivered intravenously, due to negligible intestinal absorption and its status as a p-glycoprotein substrate. After intravenous injection, vinblastine, is known to cause severe tissue irritation and even damage, which further limits its utility as a chemotherapeutic agent.

A second example involves curcumin, a compound found in turmeric extract, is a known COX-II inhibitor, prophylactic chemotherapeutic agent, histamine release inhibitor and nutritional antioxidant; however, due to p-glycoprotein catalyzed efflux <1%, of an oral dose is absorbed through the intestine. Co-administration of curcumin with the p-glycoprotein inhibitor, piperine, will only increase absorption to approximately 2.4%. The low absorption requires a larger dose of curcumin, in order to reach therapeutic concentrations in the blood stream, which makes it inconvenient for the patient to self-administer and causes an unpalatable after taste, as well as GI discomfort, discoloration of the mouth and feces.

A third example involves cannabidiol (CBD), the non-psychoactive agent found in cannabis species including industrial hemp and marijuana. CBD is also found in flax stalk, and can be legally extracted from this source. CBD is a probable anxiolytic, anticonvulsive, antispasmodic, and antipsychotic drug. It may also be useful in hospital emergency departments to relieve the dysphoric and combative symptoms associated with accidental or deliberate ingestions of some hallucinogenic drugs such as marijuana, synthetic cannabinoids (bath salts), potentially antagonists of NMDA receptors such as dextromethorphan, and agonists of 5HT-2a receptors such as mescaline and lysergic acid diethyl amide (LSD). It is approved in Canada as an anti-convulsive for pediatric use in in the treatment of a severe myoclonic epilepsy of infancy and early childhood, known as Dravet syndrome. However, at only 3% bioavailability, CBD is poorly absorbed through the intestinal lumen, despite having structural characteristics of a prototypical highly absorbent molecule. It is believed that CBD's interaction with the p-glycoprotein efflux transporter is the cause of the poor absorption; thus, by blocking this interaction, it will be possible to increase the bioavailability of a CBD oral dose. CBD is starkly expensive as an oral dosage, and alternative formulations which increase absorption would reduce the cost to patients. CBD can be administered by a nebulizer or can be smoked in order to increase the absorption. However, both of these delivery methods have drawbacks which limit their practical use. Nebulizers are expensive, inconvenient, and cannot be used discretely in public. Smoking is perceived as noxious, damaging to exposed property, socially reprehensible by most, and is invariably detrimental to the health of both the patient and bystanders. This is due to the polycyclic aromatic hydrocarbons such as benzo[a]pyrene that are produced by the burning organic material and is subsequently emitted into the air. It is reasonably presumed, therefore, that an oral dosage with good absorption, would be preferable over these alternatives by most patients.

The instant invention is a novel formulation technology which allows for effective oral absorption of low solubility, low permeability and/or p-glycoprotein efflux transporter substrate drugs and herbal extracts, such as vinblastine, curcumin, and CBD. With this technique, these are absorbed effectively through the intestinal lumen with lowered p-glycoprotein catalyzed efflux while being emulsified to compensate for problems with solubility. This technique concurrently addresses a number of formulation problems in the following manners, while the mechanism also aids absorption: 1) inhibition of intestinal p-glycoprotein, mitigating efflux of substrate drugs from enterocytes back into the intestinal lumen; 2) facilitation of mechanisms of absorption that circumvent the p-glycoprotein's reach; 3) this technique places the drug in a microemulsion on contact with water or intestinal chyme mediated by the amphipathic nature of the carbohydrate used in the formula, which has mutual affinity for the drug and the water; this compensates for poor solubility in water; and additionally 4) the drug may be drawn across membranes with the carbohydrate/alcohol formulation by means of hydrophobic affinity. The instant invention, therefore, satisfies the need for a drug substance formulation method which allows for the preparation of drug substances for oral administration, which would otherwise be ill-suited for oral dosage.

SUMMARY OF THE INVENTION

There exists many drug substances and herbal extracts which are thought to have therapeutic or other health benefits, but are not currently given as oral dosages, or are with low oral bioavailability and higher doses to compensate for this problem because they have low systemic bioavailability. Many of these drugs are expensive and the excessive dosages drive up the costs of treatment. Others which would require IV administration either have a limited market as an IV drug with a much greater market if available orally. Others currently given orally would be more marketable in a less expensive oral formulation with a lower dosage and the same effect. This problem addressed is due to having low solubility and/or low permeability, which prevents intestinal uptake; and/or they are substrates for the p-glycoprotein efflux transporter, which transports the drug substance or herbal extract back into the intestine, before it can: reach systemic circulation, become bioavailable, and reach the receptors or other target structures needed to elicit a desired clinical effect. The numbers of these drug substances and herbal remedies which have low solubility, low permeability and/or are p-glycoprotein substrates are too numerous to detail here; however, examples include: vinblastine, curcumin, cannibidiol (CBD), digoxin, loperamide, cyclosporine, tacrolimus and talinolol.

The present invention relates to an apparatus and process for formulating low solubility, low permeability and/or p-glycoprotein efflux inhibited drug substance and herbal extracts for use as oral dosages; and a composition of matter. Specifically, the present invention complexes the drug substance or herbal extract with piperine, and quercetin in a carbohydrate substrate to create a mixture that forms an emulsion on contact with water or aqueous liquids (such as gastric chyme) or forming or water soluble mixture, using a supercritical fluid or liquid gas, such as carbon dioxide, propane, nitrous oxide, cyclopropane, ethylene and substituted hydrocarbons such as halohydrocarbons to facilitate the mixture of these ingredients. The resulting mixture is highly soluble or is emulsion forming and will resist efflux back into the intestinal lumen via the p-glycoprotein efflux transporter.

DETAILED DESCRIPTION

The drug substance, herbal compound, or herbal extract (hereinafter, the API) is provided. These API materials can be of any material which is considered biopharmaceutics classification system (BCS) class III or IV, i.e. low permeability, high or low solubility and/or is a substrate for the p-glycoprotein efflux transporter.

Figure 1:
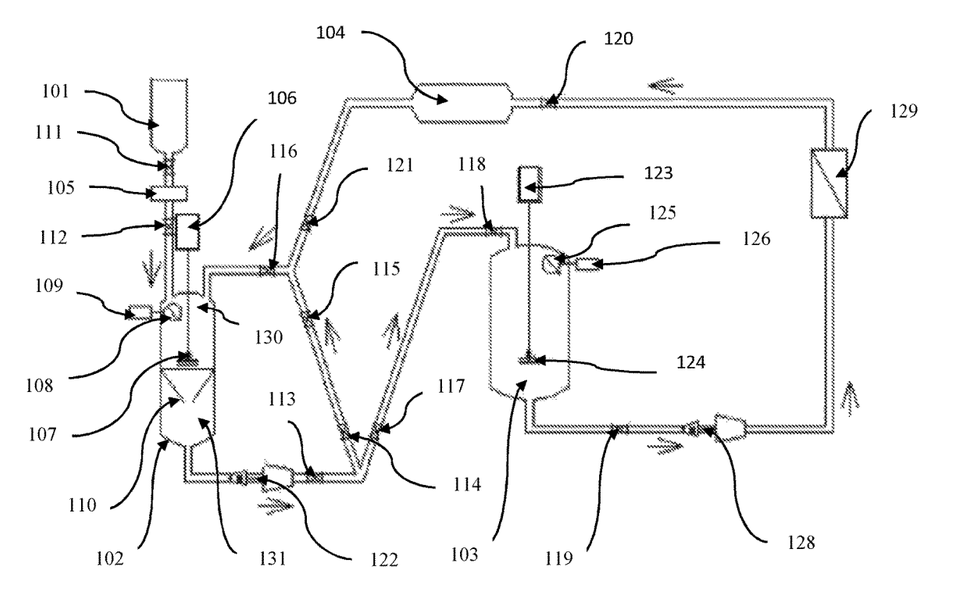
FIG. 1 is a flow chart depicting the processing of a low solubility, low permeability drug substance or herbal extract through the use of supercritical fluids and liquefied gases.

Referring now to FIG. 1, depicting a schematic view of an apparatus for complexing low, permeability, low solubility and/or p-glycoprotein substrate drug substances or herbal extracts with a carbohydrate using a supercritical fluid, liquefied compressed gases, or gas, in accordance with an example embodiment of the present invention is presented. The apparatus includes a new gas storage tank 101, an extraction processing tank 102, and an API:solvent to API: excipient transfer processing tank 103 (hereinafter "excipient transfer processing tank"). The tanks are interconnected through a system of stainless steel plumbing, compressors, and valves, which control the flow of the liquid or supercritical solvents and extracts.

Turning now to the new gas storage tank 101, which consists of a gas cylinder capable of handling temperature ranges down to near absolute zero i.e. −271° C. up to 150° C.; and a pressure ranging from near vacuum, i.e. 0.02 psi, up to 3,000 psi. The new gas storage tank 101 connects to gate valve one 111, which is then connected to an adjustable pressure regulator 105. The pressure regulator 105 reduces the gas pressure to the prescribed pressure in the procedure as it is set. The pressure regulator 105 then connects to a gate valve two 112; gate valve two 112 then attaches to the extraction processing tank 102.

The extraction processing tank 102 consists of a gas cylinder 102 capable of handling temperature ranges down to near absolute zero up to 150° C.; and a pressure ranging from near vacuum, i.e. 0.02 psi, up to 3,000 psi. The extraction processing tank 102 is segregated vertically into upper and lower partitions 130 and 131, respectively by a filtration apparatus 110 which holds a suitable filter sufficient in size to cover the surface on which the raw material will be loaded; a hatch, a homogenizer 107, comprised of a programmable motor 106 to accommodate a wide range of operating speeds as determined necessary; and a thermal regulator 108 and thermal regulator control unit 109. The filter material and porosity of the filtration apparatus 110 will vary from drug to drug and from herbal to herbal depending on the specifications of the raw material and the final product; in many cases, a commercially available 0.5 μm nylon filter is sufficient. The upper section 130 of the extraction processing tank 102 is pressurized with the gases prescribed in the material specific procedure until a supercritical fluid or liquid flows through the raw material. Some procedures will call for a gas and others will call for a liquid depending on the properties of the raw material. The fluid, now in solution with the API flows through the filtration apparatus 110 and into the lower partition 131 of the extraction processing tank 102. This fluid is then recirculated through the extraction processing tank from top to bottom and compressed back into the top of the tank via a closed loop with a compressor 122 and multiple gate valves three through six 113, 114, 115, 116. This cycle continues until the extraction commences as determined and detailed in the drug specific procedure. The gate valves 114, 115, and 116 are closed to terminate the circuit where the fluid was repeated circulated through the extraction processing tank. At this point, the fluid is a solvent:API extract and is pumped through the turbine compressor 122 through gate valve 113, which remains open and, gate valves 117 and 118 are opened, and the fluid in from the extraction processing tank containing the original liquid or supercritical gas and the extracted/dissolved API are pumped to the excipient transfer processing tank 103.

Referring now to the excipient transfer processing tank 103, which consists of a gas cylinder capable of handling temperature ranges down to near absolute zero up to 150° C.; and a pressure ranging from near vacuum, i.e. 0.02 psi, up to 3,000 psi; a hatch for loading materials for processing with a suitable safety mechanism to prevent opening while pressurized, a homogenizer 124, comprised of a programmable motor 123 to accommodate a wide range of operating speeds as determined necessary; and a thermal regulator 125 and control unit 126. The carbohydrate excipient was previously loaded into the excipient transfer processing tank 103 and if necessary, pretreated with an aqueous alcohol such as alcohol USP (90%). The carbohydrate solution is then homogenized with the homogenizer 124 and concurrently compressed by the supercritical carbon dioxide or liquid carbon dioxide and prescribed additives to the solvent:API solution resulting from the processing step that took place in the extraction processing tank which will impregnate the carbohydrate with the API, forming a slurry. Upon decompression of the supercritical fluid or liquefied gas, solid state crystals of API and carbohydrate will precipitate out of this slurry. These crystals as a delivered dose will form an emulsion in water (such as in gastric chyme in a patient's stomach) or form a solution in water.

Upon the formation of compressed API:carbohydrate mixture, the solvent is directed through gate valve nine 119, which is now opened. Gate valve 118 is closed and turbine compressor 122 is disengaged. Turbine two 128, is engaged and gate valve 120 is opened. This compresses the gas through the spent gas recovery filter 129 consisting of a suitable material such as graphite and/or silica and into the recycled gas recovery tank 104. This reduces the pressure slowly in the excipient transfer processing tank 103, where the fluid becomes a gas again. As the supercritical or liquid carbon dioxide in the excipient transfer processing tank is reduced in pressure and reverts back to gaseous state carbon dioxide, crystals of a solid mixture of the API and the carbohydrate excipient will form are will be collected for final formulation, followed by encapsulation.

The following details the preferred embodiment for this process of composing this drug delivery formulation, involving the use of liquid or supercritical fluids. First, if necessary, the drug substance, herbal, or herbal extract (hereinafter referred to as the active pharmaceutical ingredient or API), is vacuum dried, usually at <40° C. and/or pretreated with a suitable solvent such as an anhydrous alcohol, aqueous alcohol, or other suitable solvent.

Next, the API, is placed on a suitable filtration apparatus in the extraction processing tank; filter size will depend on the API and final product specifications. The extraction processing tank is compressed to a suitable pressure at a pre-determined temperature with liquid or supercritical carbon dioxide or a mixture of carbon dioxide and other suitable solvents as determined ideal for the API's physical properties. The solvent (carbon dioxide/mixture) is then circulated through the API on the filtration apparatus until the active extract is extracted suitably or the pre-extracted raw extract is dissolved fully into a compressed API:solvent.

A suitable carbohydrate such as xylitol, sucrose, or fructose, or glycerin may be pre-treated with an aqueous alcohol (i.e. 85% or 90% ethanol) and is added to the excipient transfer processing tank. The compressed API:solvent is then transferred to the excipient transfer processing tank. The compressed API:solvent, from the extraction processing tank, is compressed into the excipient transfer processing tank. The compressed API:solvent and carbohydrate excipient are homogenized and ground, as necessary with the homogenizer. The carbohydrate complexes with the API. This complex facilitates the formation of a micro-emulsion or a solution on contact with water when taken orally, increasing the solubility of the API on contact with water when administered. The spent solvent is slowly removed and compressed through a filter and other filtration as necessary and is re-compressed into a holding tank for recycling and subsequent use.

As the pressure is reduced in the excipient transfer processing tank, the solvent reverts from a liquid to a gas phase, causing the API and carbohydrate fall out of solution from the solvent and into a solid state mixture with each other, resulting in an API:carbohydrate. The API:carbohydrate is homogenized and dried of any residual water or ethanol via vacuum drying at a temperature under 40° C. and a pressure below 50 mm Hg. The process is repeated separately with the piperine and quercitin instead of API.

The API:carbohydrate, piperine:carbohydrate and quercitin:carbohydrate complexes are blended to the desired amounts. Stabilizers and emollients such as vegetable oils, waxes, lecithin, fats, semi-solid and liquid polyols, and antioxidants such as tocopherols, ascorbates, thymol, etc., may be added; as well as anti-caking agents such as corn starch, potato starch, or magnesium stearate. The final product is then encapsulated. Suitable capsules are available from many sources, and standard capsule sizes ranging from "000" to "3" are preferably used. Suitable encapsulation equipment is available from market suppliers such as Shionogi. Air can be eliminated from the capsules using an inert gas such as nitrogen.

Alternatively, the three ingredients (API, piperine, and quercetin) may be processed as above, but together made into a mixture with the carbohydrate together in one extraction rather than in making the API:Carbohydrate, piperine:carbohydrate, and quercitin:carbohydrate separately and subsequently combining them.

Throughout the process, the API or herbal extract, piperine, or bioperine and quercitin are monitored for their concentration levels. The methodology for measuring the concentration levels may change from herbal extract to herbal extract or API to API as appropriate per compendial analytical practices, such as found in the USP guidelines. A trained natural products or pharmaceutical chemist develops the methodology or uses accepted reference methodologies in accordance with 21 CFR part 111 subpart J and other relevant regulations and standards.

EXAMPLES

The following specific examples are provided to afford a better understanding of the present invention to those skilled in the art. It is to be understood that these samples are intended to be illustrative only and are not intended to limit the invention in any way.

Example 1

Preparation of Vinblastine Oral Modified Release with Supercritical $CO_2$:
  A) Preparation of Vinblastine:Sucrose Crystals
    1. Weigh out 1.25 g of raw vinblastine (API).
    2. If necessary, vacuum dry the API at a temperature of 39° C. at a pressure of <50 mm Hg for 5 hours.

3. Pre-treat the raw vinblastine with a mixture of 95% ethanol: 5% water with ammonia to a PH of 9.8 to equal the weight of the raw material.
4. API is placed in the loading area of the extraction processing tank.
5. The extraction processing tank of 1 L in volume is compressed to 1200 PSI at a temperature of 35° C. with a supercritical solvent consisting of 99% carbon dioxide and 1% of the following additive: 95% aqueous solution of alcohol USP with ammonia to a PH of 9.8.
6. The agitator in the extraction processing tank shall be engaged at a speed of approximately 500 RPM.
7. Compress the supercritical carbon dioxide solvent through the raw API and subsequently through the filtration apparatus upon which it rests (a 0.5 µm nylon filter) at a flow rate of 20 linear inches/min.
8. Recirculate the collected solvent and dissolved raw material through extraction tank for 5 minutes; once completed this material is compressed API:solvent.
9. Load the excipient transfer processing tank with 3.7 g of sucrose USP.
10. Equilibrate the excipient phase transfer processing tank, 10 liters in volume, 1200 PSI at a temperature of 35° C. with a supercritical solvent consisting of 99% CO2 and 1% of the following additive: 95% aqueous solution of alcohol USP.
11. Pump the API:solvent solution produced in the extraction processing tank into the excipient transfer processing tank.
12. Repeat steps (3)-(8) and (11) until the all raw material and residue thereof is fully dissolved and transferred to the excipient transfer tank.
13. Set the agitator in the excipient transfer processing tank speed to 2000 RPM and homogenize
14. Once a solution is formed and the excipient is fully dissolved, pressure is decreased at a rate of 20 PSI/min, with the temperature maintained constantly until the solvent becomes a gas and solid crystals of API:sucrose have formed.
15. The excipient transfer processing tank is then equilibrated to ±1 psi of atmospheric pressure at room temperature, as necessary, to safely open the tank and remove the crystals of API:sucrose.
16. The API:sucrose may be dried if necessary by means of vacuum drying at a temperature of 39° C. and a pressure of <50 mmHg for 5 hours before or after removal from the tank.
17. Remove the vinblastine:sucrose crystals.
18. The spent solvent is recovered and pumped through a graphite and silica filter.
19. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual vinblastine. The solvent is continually recovered per step (18).

B) Preparation of Piperine:Sucrose Crystals

20. Treat 2 g of piperine or a botanical source containing 2 g thereof with 1 mL of alcohol USP.
21. Place the treated piperine or botanical source previously treated in the loading area of the extraction processing tank of 1 L in volume.
22. The extraction processing tank is compressed to 1200 psi at a temperature of 35° C. with a supercritical solvent consisting of 100% carbon dioxide.
23. Engage the extraction processing tank agitator at a speed of approximately 500 RPM.
24. Compress the supercritical carbon dioxide solvent through the raw piperine and subsequently through the 0.5 µm nylon filter upon which it rests at a flow rate of 20 linear inches/min.
25. Recirculate the collected solvent and dissolved raw material through this apparatus for 5 minutes.
26. Load a 10 L excipient transfer processing tank with 5.71 g of sucrose USP.
27. Pump the piperine:solvent solution produced in the extraction processing tank into the excipient transfer processing tank, equilibrated to 1200 PSI at a temperature of 35° C. with a supercritical solvent consisting of 100% carbon dioxide.
28. Pump the piperine:solvent solution formed in step (25) excipient transfer processing tank.
29. Repeat steps (22)-(25); (28) until the piperine and all residue thereof is in the excipient transfer processing tank.
30. Set the excipient transfer processing tank agitator to a speed of 2000 RPM.
31. Once a solution is formed and the excipient is fully dissolved, pressure is decreased at a rate of 20 psi/min, with the temperature maintained constantly until the solvent becomes a gas and the solid crystals of Piperine:excipient have formed.
32. Equilibrate the excipient transfer processing tank to ±1 psi of atmospheric pressure and room temperature, as necessary, to safely open the tank and remove the crystals of piperine:sucrose.
33. Vacuum dry the piperine:sucrose at a temperature of 39° C. and a pressure of <50 mm Hg for 5 hours before or after removal from the tank.
34. Remove the piperine:sucrose crystals from the tank.
35. The spent solvent is recovered and pumped through a graphite and silica filter.
36. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual piperine. The solvent is continually recovered per step (35).

C) Preparation of Quercitin:Sucrose Crystals

37. Vacuum dry quercetin or a botanical source of quercetin at 39° C. and a pressure of <50 mmHg for 5 hours.
38. The raw quercetin is weighed to 50 g of quercetin or the equivalent of a botanical source containing 50 g of quercetin.
39. Treat the dried quercitin with 25 ml of 50% aqueous solution of alcohol USP.
40. Load the dried quercitin into the loading area of a 1 L extraction processing tank.
41. The extraction processing tank is compressed to 1200 PSI at a temperature of 35° C. with a supercritical solvent consisting of 95% carbon dioxide and 5% of the following additive: 70% aqueous solution of alcohol USP.
42. Engage the extraction processing tank agitator at a speed of approximately 500 RPM.
43. The supercritical solvent is compressed through the quercitin and subsequently through the 0.5 µm nylon filter upon which it rests, at a flow rate of 20 linear inches/min.
44. Recirculate the collected solvent and dissolved quercitin the apparatus for 10 minutes.

45. Load a 50 L excipient transfer processing tank with 142.7 g of sucrose.
46. Equilibrate the excipient transfer processing tank to 1200 psi at a temperature of 35° C. with a supercritical solvent consisting of 95% carbon dioxide and 5% of the following additive: a 70% solution of alcohol USP.
47. Pump the quercitin:solvent solution produced in the extraction processing tank into the excipient transfer processing tank.
48. Set the excipient transfer processing tank agitator to a speed of 2000 RPM.
49. Repeat steps 40-44 and 47 until all of the quercetin and residue thereof is dissolved fully and is transferred to the excipient transfer processing tank.
50. Once a solution is formed and the excipient is fully dissolved, decrease the pressure at a rate of 20 PSI/min, with the temperature maintained constantly, until the solvent becomes a gas and the solid crystals of quercitin:sucrose have formed.
51. Equilibrate the excipient transfer processing tank to ±1 psi of atmospheric pressure and room temperature, as necessary, to safely open the tank and remove the crystals of quercetin:sucrose.
52. Remove the quercitin:sucrose crystals and vacuum dry them at 39° C. and a pressure of <50 mm Hg for five hours.
53. The spent solvent is recovered and pumped through a graphite and silica filter.
54. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual vinblastine. The solvent is continually recovered per step (53).

D) Final Processing and Encapsulation

55. Prepare the final product by blending the vinblastine:sucrose with the piperine:sucrose and quercetin:sucrose, as well as addition of stabilizers and emollients such as vegetable oils, waxes, lecithin, fats, semi-solid and liquid polyols, and antioxidants such as tocopherols, ascorbates, thymol, etc. Anti-caking agents such as corn starch, potato starch, or magnesium stearate may also be added.
56. Encapsulate the final product using standard encapsulation equipment such as those made by Shionogi in size 3 capsules; the finished product will contain 1.25 mg of the drug vinblastine, 2 mg of piperine, and 50 mg of quercetin and approximately 200 mg of sucrose base per capsule.

Example 2

Preparation of Curcumin Oral Modified Release with Supercritical $CO_2$:

A) Preparation of Curcumin:Xylitol Crystals

1. Weigh out 10 g of raw curcumin or a raw botanical material containing 10 g of curcumin (API).
2. If necessary, vacuum dry the API at a temperature of 39° C. at a pressure of <50 mm Hg for 5 hours.
3. API is placed in the loading area of the extraction processing tank.
4. The extraction processing tank of 1 L in volume is compressed to 1200 PSI at a temperature of 35° C. with a supercritical solvent consisting of 95% carbon dioxide and 5% of a 70% aqueous solution alcohol USP.
5. The agitator in the extraction processing tank shall be engaged at a speed of approximately 500 RPM.
6. Compress the supercritical carbon dioxide solvent through the raw API and subsequently, through the filtration apparatus upon which it rests (a 0.5 μm nylon filter) at a flow rate of 20 linear inches/min.
7. Recirculate the collected solvent and dissolved raw material through extraction tank for 5 minutes; once completed this material is compressed API:solvent.
8. Load the excipient transfer processing tank with 39.33 g xylitol.
9. Equilibrate the excipient phase transfer processing tank, 10 liters in volume, 1200 PSI at a temperature of 35° C. with a supercritical solvent consisting of 99% CO2 and 1% of the following additive: 95% aqueous solution of alcohol USP.
10. Pump the API:solvent solution produced in the extraction processing tank into the excipient transfer processing tank.
11. Repeat steps (4)-(7) and (10) until the all raw material and residue thereof is fully dissolved and transferred to the excipient transfer tank.
12. Set the agitator in the excipient transfer processing tank speed to 2000 RPM to homogenize
13. Once a solution is formed and the excipient is fully dissolved, pressure is decreased at a rate of 20 PSI/min, with the temperature maintained constantly until the solvent becomes a gas and solid crystals of API:xylitol have formed.
14. The excipient transfer processing tank is then equilibrated to ±1 PSI of atmospheric pressure at room temperature, as necessary, to safely open the tank and remove the crystals of API:xylitol.
15. The API:xylitol may be dried if necessary by means of vacuum drying at a temperature of 39° C. and a pressure of <50 mmHg for 5 hours before or after removal from the tank.
16. Remove the API:xylitol crystals.
17. The spent solvent is recovered and pumped through a graphite and silica filter.
18. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual curcumin. The solvent is continually recovered per step (18).

B) Preparation of Piperine:Xylitol Crystals

19. Weigh out 5 g of piperine or a botanical source containing 5 g thereof
20. If necessary, vacuum dry the piperine at a temperature of 39° C. at a pressure of <50 mm Hg for 5 hours.
21. Piperine is placed in the loading area of the extraction processing tank.
22. The extraction processing tank is compressed to 1200 psi at a temperature of 35° C. with a supercritical solvent consisting of 100% carbon dioxide.
23. Engage the extraction processing tank agitator at a speed of approximately 500 RPM.
24. Compress the supercritical carbon dioxide solvent through the raw piperine and subsequently through the 0.5 μm nylon filter upon which it rests at a flow rate of 20 linear inches/min.
25. Recirculate the collected solvent and dissolved raw material through this apparatus for 5 minutes.
26. Load a 10 L excipient transfer processing tank with 39.33 of xylitol.

27. Pump the piperine:solvent solution produced in the extraction processing tank into the excipient transfer processing tank, equilibrated to 1200 PSI at a temperature of 35° C. with a supercritical solvent consisting of 97% carbon dioxide and 3% of a solution of 70% aqueous alcohol USP.
28. Pump the piperine:solvent solution formed in step (25) to the excipient transfer processing tank.
29. Repeat steps (22)-(25); (28) until the piperine and all residue thereof is in the excipient transfer processing tank.
30. Set the excipient transfer processing tank agitator to a speed of 2000 RPM.
31. Once a solution is formed and the excipient is fully dissolved, pressure is decreased at a rate of 20 PSI/min, with the temperature maintained constantly until the solvent becomes a gas and the solid crystals of piperine:xylitol have formed.
32. Equilibrate the excipient transfer processing tank to ±1 PSI of atmospheric pressure and room temperature, as necessary, to safely open the tank and remove the crystals of piperine:xylitol.
33. Vacuum dry the piperine:xylitol at a temperature of 39° C. and a pressure of <50 mm Hg for 5 hours before or after removal from the tank.
34. Remove the piperine:xylitol crystals from the tank.
35. The spent solvent is recovered and pumped through a graphite and silica filter.
36. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual piperine. The solvent is continually recovered per step (35).

C) Preparation of Quercitin:Xylitol Crystals

37. Weigh out 75 g of quercitin or a botanical source containing 75 g thereof
38. If necessary, vacuum dry the quercitin at a temperature of 39° C. at a pressure of <50 mm Hg for 5 hours. Vacuum dry quercetin or a botanical source of quercetin at 39° C. and a pressure of <50 mm Hg for 5 hours.
39. The extraction processing tank is compressed to 1200 PSI at a temperature of 35° C. with a supercritical solvent consisting of 95% carbon dioxide and 5% of the following additive: 70% aqueous solution of alcohol USP.
40. Engage the extraction processing tank agitator at a speed of approximately 500 RPM.
41. The supercritical solvent is compressed through the quercitin and subsequently through the 0.5 μm nylon filter upon which it rests, at a flow rate of 20 linear inches/min.
42. Recirculate the collected solvent and dissolved quercitin in the apparatus for 10 minutes.
43. Load a 50 L excipient transfer processing tank with 39.33 g of xylitol.
44. Equilibrate the excipient transfer processing tank to 1200 PSI at a temperature of 35° C. with a supercritical solvent consisting of 95% carbon dioxide and 5% of the following additive: a 70% solution of alcohol USP.
45. Pump the quercitin: solvent solution produced in the extraction processing tank into the excipient transfer processing tank.
46. Set the excipient transfer processing tank agitator to a speed of 2000 RPM.
47. Repeat steps (39)-(42) and (45) until all of the quercetin and residue thereof is dissolved fully and is transferred to the excipient transfer processing tank.
48. Once a solution is formed and the excipient is fully dissolved, decrease the pressure at a rate of 20 PSI/min, with the temperature maintained constantly, until the solvent becomes a gas and the solid crystals of quercitin: xylitol have formed.
49. Equilibrate the excipient transfer processing tank to ±1 PSI of atmospheric pressure and room temperature, as necessary, to safely open the tank and remove the crystals of quercetin:xylitol.
50. Remove the quercitin: xylitol crystals and vacuum dry them at 39° C. and a pressure of <50 mm Hg for five hours.
51. The spent solvent is recovered and pumped through a graphite and silica filter.
52. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual curcumin. The solvent is continually recovered per step (51).

D) Final Processing and Encapsulation

53. Prepare the final product by blending the curcumin: xylitol with the piperine:xylitol and quercetin:xylitol, as well as addition of stabilizers and emollients such as vegetable oils, waxes, lecithin, fats, semi-solid and liquid polyols, and antioxidants such as tocopherols, ascorbates, thymol, etc. Anti-caking agents such as corn starch, potato starch, or magnesium stearate may also be added.
54. Encapsulate the final product using standard encapsulation equipment such as those made by Shionogi in size 00 capsules; the finished product will contain 10 mg of the drug curcumin, 5 mg of piperine, and 75 mg of quercetin and approximately 750 mg of xylitol base per capsule.

Example 3

Preparation of Cannabidiol (CBD) Oral Modified Release with Supercritical $CO_2$:

A) Preparation of CBD:Sucrose Crystals

1. Weigh out 10 g of raw CBD or a raw botanical material containing 10 g of CBD (API).
2. If necessary, vacuum dry the API at a temperature of 39° C. at a pressure of <50 mm Hg for 5 hours.
3. API is placed in the loading area of the extraction processing tank.
4. The extraction processing tank of 1 L in volume is compressed to 1200 PSI at a temperature of 35° C. with a supercritical solvent consisting of 95% carbon dioxide and 5% of a 70% aqueous solution alcohol USP.
5. The agitator in the extraction processing tank shall be engaged at a speed of approximately 500 RPM.
6. Compress the supercritical carbon dioxide solvent through the raw API and subsequently, through the filtration apparatus upon which it rests (a 0.5 μm nylon filter) at a flow rate of 20 linear inches/min.
7. Recirculate the collected solvent and dissolved raw material through extraction tank for 5 minutes.
8. Load the excipient transfer processing tank with 39.34 g sucrose.
9. Equilibrate the excipient phase transfer processing tank, 10 liters in volume, 1200 PSI at a temperature of 35° C. with a supercritical solvent consisting of 99% CO2 and 1% of a 95% aqueous ethanol solution at PH 11.7.

10. Pump the API:solvent solution produced in the extraction processing tank into the excipient transfer processing tank.
11. Repeat steps (4)-(7) and (10) until the all raw material and residue thereof is fully dissolved and transferred to the excipient transfer tank.
12. Set the agitator in the excipient transfer processing tank speed to 2000 RPM and homogenize.
13. Once a solution is formed and the excipient is fully dissolved, pressure is decreased at a rate of 20 PSI/min, with the temperature maintained constantly until the solvent becomes a gas and solid crystals of API:sucrose have formed.
14. The excipient transfer processing tank is then equilibrated to ±1 PSI of atmospheric pressure at room temperature, as necessary, to safely open the tank and remove the crystals of API:sucrose.
15. The API:sucrose may be dried if necessary by means of vacuum drying at a temperature of 39° C. and a pressure of <50 mmHg for 5 hours before or after removal from the tank.
16. Remove the API:sucrose crystals.
17. The spent solvent is recovered and pumped through a graphite and silica filter.
18. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual CBD. The solvent is continually recovered per step (17).

B) Preparation of Piperine:Sucrose Crystals

19. Weigh out 5 g of piperine or a botanical source containing 5 g thereof
20. If necessary, vacuum dry the piperine at a temperature of 39° C. at a pressure of <50 mm Hg for 5 hours.
21. Piperine is placed in the loading area of the extraction processing tank.
22. The extraction processing tank is compressed to 1200 psi at a temperature of 35° C. with a supercritical solvent consisting of 100% carbon dioxide.
23. Engage the extraction processing tank agitator at a speed of approximately 500 RPM.
24. Compress the supercritical carbon dioxide solvent through the raw piperine and subsequently through the 0.5 μm nylon filter upon which it rests at a flow rate of 20 linear inches/min.
25. Recirculate the collected solvent and dissolved raw material through this apparatus for 5 minutes.
26. Load a 10 L excipient transfer processing tank with 39.34 of sucrose.
27. Pump the piperine:solvent solution produced in the extraction processing tank into the excipient transfer processing tank, equilibrated to 1200 PSI at a temperature of 35° C. with a supercritical solvent consisting of 100% carbon dioxide.
28. Pump the piperine:solvent solution formed in step (25) to the excipient transfer processing tank.
29. Repeat steps (22)-(25) and (28) until the piperine and all residue thereof is in the excipient transfer processing tank.
30. Set the excipient transfer processing tank agitator to a speed of 2000 RPM.
31. Once a solution is formed and the excipient is fully dissolved, pressure is decreased at a rate of 20 PSI/min, with the temperature maintained constantly until the solvent becomes a gas and the solid crystals of piperine:sucrose have formed.
32. Equilibrate the excipient transfer processing tank to ±1 PSI of atmospheric pressure and room temperature, as necessary, to safely open the tank and remove the crystals of piperine:sucrose.
33. Vacuum dry the piperine:sucrose at a temperature of 39° C. and a pressure of <50 mm Hg for 5 hours before or after removal from the tank.
34. Remove the piperine:sucrose crystals from the tank.
35. The spent solvent is recovered and pumped through a graphite and silica filter.
36. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual piperine. The solvent is continually recovered per step (35).

C) Preparation of Quercitin:Sucrose Crystals

37. Weigh out 75 g of quercitin or a botanical source containing 75 g thereof
38. If necessary, vacuum dry the quercitin at a temperature of 39° C. at a pressure of <50 mm Hg for 5 hours. Vacuum dry quercetin or a botanical source of quercetin at 39° C. and a pressure of <50 mm Hg for 5 hours.
39. The extraction processing tank is compressed to 1200 PSI at a temperature of 35° C. with a supercritical solvent consisting of 95% carbon dioxide and 5% of the following additive: 70% aqueous solution of alcohol USP.
40. Engage the extraction processing tank agitator at a speed of approximately 500 RPM.
41. The supercritical solvent is compressed through the quercitin and subsequently through the 0.5 μm nylon filter upon which it rests, at a flow rate of 20 linear inches/min.
42. Recirculate the collected solvent and dissolved quercitin in the apparatus for 10 minutes.
43. Load a 50 L excipient transfer processing tank with 39.33 g of sucrose.
44. Equilibrate the excipient transfer processing tank to 1200 PSI at a temperature of 35° C. with a supercritical solvent consisting of 95% carbon dioxide and 5% of the following additive: a 70% solution of alcohol USP.
45. Pump the quercitin: solvent solution produced in the extraction processing tank into the excipient transfer processing tank.
46. Set the excipient transfer processing tank agitator to a speed of 2000 RPM.
47. Repeat steps (39)-(42) and 45 until all of the quercetin and residue thereof is dissolved fully and is transferred to the excipient transfer processing tank.
48. Once a solution is formed and the excipient is fully dissolved, decrease the pressure at a rate of 20 PSI/min, with the temperature maintained constantly, until the solvent becomes a gas and the solid crystals of quercitin: sucrose have formed.
49. Equilibrate the excipient transfer processing tank to ±1 PSI of atmospheric pressure and room temperature, as necessary, to safely open the tank and remove the crystals of quercetin:sucrose.

50. Remove the quercitin:sucrose crystals and vacuum dry them at 39° C. and a pressure of <50 mm Hg for five hours.
51. The spent solvent is recovered and pumped through a graphite and silica filter.
52. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual CBD. The solvent is continually recovered per step (51).

D) Final Processing and Encapsulation

53. Prepare the final product by blending the crystals of CBD:sucrose with the piperine:sucrose and quercetin:sucrose, as well as addition of stabilizers and emollients such as vegetable oils, waxes, lecithin, fats, semi-solid and liquid polyols, and antioxidants such as tocopherols, ascorbates, thymol, etc. Anti-caking agents such as corn starch, potato starch, or magnesium stearate may also be added.
54. Encapsulate the final product using standard encapsulation equipment such as those made by Shionogi in size 0 capsules; the finished product will contain 10 mg of the drug CBD, 5 mg of piperine, and 75 mg of quercetin and approximately 500 mg of sucrose base per capsule.

Example 4

Preparation of Digoxin Oral Modified Release with Liquid and Supercritical $CO_2$:

A) Preparation of Digoxin:Xylitol Crystals

1. Weigh out 875 mg of raw digoxin or a raw botanical material containing digitalis lantana equivalent to 875 mg raw digoxin (API).
2. If necessary, vacuum dry the API at a temperature of 39° C. at a pressure of <50 mm Hg for 5 hours.
3. API is placed in the loading area of the extraction processing tank.
4. Pre-treat the raw dioxin with a mixture of 95% aqueous ethanol, adjusted to a PH of 5.0 with acetic acid, to equal the weight of the raw material.
5. The extraction processing tank of 1 L in volume is compressed to 170 PSI at a temperature of −50° C. with a liquid solvent consisting of 99% CO2 and 1% of a 95% aqueous ethanol solution, adjusted to PH 5 with acetic acid.
6. The agitator in the extraction processing tank shall be engaged at a speed of approximately 500 RPM.
7. Compress the liquid carbon dioxide solvent through the raw API and subsequently, through the filtration apparatus upon which it rests (a 0.5 μm nylon filter) at a flow rate of 20 linear inches/min.
8. Recirculate the collected solvent and dissolved raw material through extraction tank for 5 minutes; once completed this material is compressed API:solvent.
9. Load the excipient transfer processing tank with 2.40 g xylitol.
10. Equilibrate the excipient phase transfer processing tank, 10 liters in volume, 1200 PSI at a temperature of 35° C. with a liquid solvent consisting of 99% CO2 and 1% of a 95% aqueous ethanol solution at PH 11.7.
11. Pump the API:solvent solution produced in the extraction processing tank into the excipient transfer processing tank.
12. Repeat steps (5)-(8) and (11) until the all raw material and residue thereof is fully dissolved and transferred to the excipient transfer tank.
13. Set the agitator in the excipient transfer processing tank speed to 2000 RPM and homogenize.
14. Once a solution is formed and the excipient is fully dissolved, pressure is decreased at a rate of 20 PSI/min, with the temperature maintained constantly until the solvent becomes a gas and solid crystals of API:xylitol have formed.
15. The excipient transfer processing tank is then equilibrated to ±1 PSI of atmospheric pressure at room temperature, as necessary, to safely open the tank and remove the crystals of API:xylitol.
16. The API:xylitol may be dried if necessary by means of vacuum drying at a temperature of 39° C. and a pressure of <50 mm Hg for 5 hours before or after removal from the tank.
17. Remove the API:xylitol crystals.
18. The spent solvent is recovered and pumped through a graphite and silica filter.
19. The apparatus as a whole (extraction processing tank, excipient transfer processing tank, and all plumbing) is repeatedly flushed with liquid carbon dioxide and/or liquid carbon dioxide until all residue from the process is removed and the apparatus is tested negative for residual digoxin. The solvent is continually recovered per step (18).

B) Preparation of Piperine:Xylitol Crystals

20. Treat 2 g of piperine or a botanical source containing 2 g thereof with 1 mL of alcohol USP.
21. Place the treated piperine or botanical source previously treated in the loading area of the extraction processing tank of 1 L in volume.
22. The extraction processing tank is compressed to 1200 psi at a temperature of 35° C. with a supercritical solvent consisting of 100% carbon dioxide.
23. Engage the extraction processing tank agitator at a speed of approximately 500 RPM.
24. Compress the supercritical carbon dioxide solvent through the raw piperine and subsequently through the 0.5 μm nylon filter upon which it rests at a flow rate of 20 linear inches/min.
25. Recirculate the collected solvent and dissolved raw material through this apparatus for 5 minutes.
26. Load a 10 L excipient transfer processing tank with 5.71 g of xylitol USP.
27. Pump the piperine:solvent solution produced in the extraction processing tank into the excipient transfer processing tank, equilibrated to 1200 PSI at a temperature of 35° C. with a supercritical solvent consisting of 100% carbon dioxide.
28. Repeat steps (22)-(25) and (27) until the piperine and all residue thereof is in the excipient transfer processing tank.
29. Set the excipient transfer processing tank agitator to a speed of 2000 RPM.
30. Once a solution is formed and the excipient is fully dissolved, pressure is decreased at a rate of 20 psi/min, with the temperature maintained constantly until the solvent becomes a gas and the solid crystals of Piperine:excipient have formed.
31. Equilibrate the excipient transfer processing tank to ±1 psi of atmospheric pressure and room temperature, as necessary, to safely open the tank and remove the crystals of piperine:xylitol.

32. Vacuum dry the piperine:xylitol at a temperature of 39° C. and a pressure of <50 mm Hg for 5 hours before or after removal from the tank.
33. Remove the piperine:xylitol crystals from the tank.
34. The spent solvent is recovered and pumped through a graphite and silica filter.
35. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual piperine. The solvent is continually recovered per step (34).

C) Preparation of Quercitin:Xylitol Crystals

36. Vacuum dry quercetin or a botanical source of quercetin at 39° C. and a pressure of <50 mmHg for 5 hours.
37. The raw quercetin is weighed to 50 g of quercetin or the equivalent of a botanical source containing 50 g of quercetin.
38. Treat the dried quercitin with 25 ml of 50% aqueous solution of alcohol USP.
39. Load the dried quercitin into the loading area of a 1 L extraction processing tank.
40. The extraction processing tank is compressed to 1200 PSI at a temperature of 35° C. with a supercritical solvent consisting of 95% carbon dioxide and 5% of the following additive: 70% aqueous solution of alcohol USP.
41. Engage the extraction processing tank agitator at a speed of approximately 500 RPM.
42. The supercritical solvent is compressed through the quercitin and subsequently through the 0.5 μm nylon filter upon which it rests, at a flow rate of 20 linear inches/min.
43. Recirculate the collected solvent and dissolved quercitin the apparatus for 10 minutes.
44. Load a 50 L excipient transfer processing tank with 142.7 g of xylitol.
45. Equilibrate the excipient transfer processing tank to 1200 psi at a temperature of 35° C. with a supercritical solvent consisting of 95% carbon dioxide and 5% of the following additive: a 70% aqueous solution of alcohol USP.
46. Pump the quercitin: solvent solution produced in the extraction processing tank into the excipient transfer processing tank.
47. Set the excipient transfer processing tank agitator to a speed of 2000 RPM.
48. Repeat steps (40)-(43) and (46) until all of the quercetin and residue thereof is dissolved fully and is transferred to the excipient transfer processing tank.
49. Once a solution is formed and the excipient is fully dissolved, decrease the pressure at a rate of 20 PSI/min, with the temperature maintained constantly, until the solvent becomes a gas and the solid crystals of quercitin: sucrose have formed.
50. Equilibrate the excipient transfer processing tank to ±1 psi of atmospheric pressure and room temperature, as necessary, to safely open the tank and remove the crystals of quercetin:sucrose.
51. Remove the quercitin: xylitol crystals and vacuum dry them at 39° C. and a pressure of <50 mm Hg for five hours.
52. The spent solvent is recovered and pumped through a graphite and silica filter.
53. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual quercetin. The solvent is continually recovered per step (52).

D) Final Processing and Encapsulation

54. Prepare the final product by blending the digoxin: xylitol with the piperine:xylitol and quercetin:xylitol, as well as addition of stabilizers and emollients such as vegetable oils, waxes, lecithin, fats, semi-solid and liquid polyols, and antioxidants such as tocopherols, ascorbates, thymol, etc. Anti-caking agents such as corn starch, potato starch, or magnesium stearate may also be added.
55. Encapsulate the final product using standard encapsulation equipment such as those made by Shionogi in size 3 capsules; the finished product will contain 87.5 μg of the drug digoxin, 5 mg of piperine, and 50 mg of quercetin and approximately 200 mg of xylitol base per capsule.

Example 5

Preparation of Loperamide Oral Modified Release with Liquid and Supercritical $CO_2$:

A) Preparation of Loperamide:Xylitol Crystals

1. Weigh out 875 mg of raw loperamide
2. If necessary, vacuum dry the API at a temperature of 39° C. at a pressure of <50 mm Hg for 5 hours.
3. API is placed in the loading area of the extraction processing tank.
4. The extraction processing tank of 1 L in volume is compressed to 170 PSI at a temperature of −50° C. with a liquid solvent consisting of 99% CO2 and 1% of a 95% aqueous ethanol, PH of 12.
5. The agitator in the extraction processing tank shall be engaged at a speed of approximately 500 RPM.
6. Compress the liquid carbon dioxide solvent through the raw API and subsequently, through the filtration apparatus upon which it rests (a 0.5 μm nylon filter) at a flow rate of 20 linear inches/min.
7. Recirculate the collected solvent and dissolved raw material through extraction tank for 5 minutes; once completed this material is compressed API:solvent.
8. Load the excipient transfer processing tank with 6.76 g xylitol.
9. Equilibrate the excipient phase transfer processing tank, 10 liters in volume, 1200 PSI at a temperature of 35° C. with a liquid solvent consisting of 99% CO2 and 1% of a 95% aqueous ethanol solution at PH 12.0.
10. Pump the API:solvent solution produced in the extraction processing tank into the excipient transfer processing tank.
11. Repeat steps (4)-(7) and (10) until the all raw material and residue thereof is fully dissolved and transferred to the excipient transfer tank.
12. Set the agitator in the excipient transfer processing tank speed to 2000 RPM and homogenize.
13. Once a solution is formed and the excipient is fully dissolved, pressure is decreased at a rate of 20 PSI/min, with the temperature maintained constantly until the solvent becomes a gas and solid crystals of API:xylitol have formed.
14. The excipient transfer processing tank is then equilibrated to ±1 PSI of atmospheric pressure at room temperature, as necessary, to safely open the tank and remove the crystals of API:xylitol.

15. The API:xylitol may be dried if necessary by means of vacuum drying at a temperature of 39° C. and a pressure of <50 mm Hg for 5 hours before or after removal from the tank.
16. Remove the API:xylitol crystals.
17. The spent solvent is recovered and pumped through a graphite and silica filter.
18. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual loperamide. The solvent is continually recovered per step (17).

B) Preparation of Piperine:Xylitol Crystals

19. Treat 2 g of piperine or a botanical source containing 2 g thereof with 1 mL of alcohol USP.
20. Place the treated piperine or botanical source previously treated in the loading area of the extraction processing tank of 1 L in volume.
21. The extraction processing tank is compressed to 1200 psi at a temperature of 35° C. with a supercritical solvent consisting of 100% carbon dioxide.
22. Engage the extraction processing tank agitator at a speed of approximately 500 RPM.
23. Compress the supercritical carbon dioxide solvent through the raw piperine and subsequently through the 0.5 μm nylon filter upon which it rests at a flow rate of 20 linear inches/min.
24. Recirculate the collected solvent and dissolved raw material through this apparatus for 5 minutes.
25. Load a 10 L excipient transfer processing tank with 5.71 g of xylitol.
26. Pump the piperine:solvent solution produced in the extraction processing tank into the excipient transfer processing tank, equilibrated to 1200 PSI at a temperature of 35° C. with a supercritical solvent consisting of 100% carbon dioxide.
27. Repeat steps (21)-(24) and (26) until the piperine and all residue thereof is in the excipient transfer processing tank.
28. Set the excipient transfer processing tank agitator to a speed of 2000 RPM.
29. Once a solution is formed and the excipient is fully dissolved, pressure is decreased at a rate of 20 psi/min, with the temperature maintained constantly until the solvent becomes a gas and the solid crystals of Piperine:excipient have formed.
30. Equilibrate the excipient transfer processing tank to ±1 psi of atmospheric pressure and room temperature, as necessary, to safely open the tank and remove the crystals of piperine:xylitol.
31. Vacuum dry the piperine:sucrose at a temperature of 39° C. and a pressure of <50 mm Hg for 5 hours before or after removal from the tank.
32. Remove the piperine:xylitol crystals from the tank.
33. The spent solvent is recovered and pumped through a graphite and silica filter.
34. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual piperine. The solvent is continually recovered per step (35).

C) Preparation of Quercitin:Xylitol Crystals

35. Vacuum dry quercetin or a botanical source of quercetin at 39° C. and a pressure of <50 mmHg for 5 hours.
36. The raw quercetin is weighed to 50 g of quercetin or the equivalent of a botanical source containing 50 g of quercetin.
37. Treat the dried quercitin with 25 ml of 50% aqueous solution of alcohol USP.
38. Load the dried quercitin into the loading area of a 1 L extraction processing tank.
39. The extraction processing tank is compressed to 1200 PSI at a temperature of 35° C. with a supercritical solvent consisting of 95% carbon dioxide and 5% of the following additive: 70% aqueous solution of alcohol USP.
40. Engage the extraction processing tank agitator at a speed of approximately 500 RPM.
41. The supercritical solvent is compressed through the quercitin and subsequently through the 0.5 μm nylon filter upon which it rests, at a flow rate of 20 linear inches/min.
42. Recirculate the collected solvent and dissolved quercitin the apparatus for 10 minutes.
43. Load a 50 L excipient transfer processing tank with 142.7 g of xylitol.
44. Equilibrate the excipient transfer processing tank to 1200 psi at a temperature of 35° C. with a supercritical solvent consisting of 95% carbon dioxide and 5% of the following additive: a 70% solution of alcohol USP.
45. Pump the quercitin: solvent solution produced in the extraction processing tank into the excipient transfer processing tank.
46. Set the excipient transfer processing tank agitator to a speed of 2000 RPM.
47. Repeat steps (39)-(42) and (45) until all of the quercetin and residue thereof is dissolved fully and is transferred to the excipient transfer processing tank.
48. Once a solution is formed and the excipient is fully dissolved, decrease the pressure at a rate of 20 PSI/min, with the temperature maintained constantly, until the solvent becomes a gas and the solid crystals of quercitin: xylitol have formed.
49. Equilibrate the excipient transfer processing tank to ±1 psi of atmospheric pressure and room temperature, as necessary, to safely open the tank and remove the crystals of quercitin:xylitol.
50. Remove the quercitin: xylitol crystals and vacuum dry them at 39° C. and a pressure of <50 mm Hg for five hours.
51. The spent solvent is recovered and pumped through a graphite and silica filter.
52. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual quercetin. The solvent is continually recovered per step (51).

D) Final Processing and Encapsulation

53. Prepare the final product by blending the loperamide:xylitol with the piperine:xylitol, and quercetin:xylitol, as well as addition of stabilizers and emollients such as vegetable oils, waxes, lecithin, fats, semi-solid and liquid polyols, and antioxidants such as tocopherols, ascorbates, thymol, etc. Anti-caking agents such as corn starch, potato starch, or magnesium stearate may also be added.

54. Encapsulate the final product using standard encapsulation equipment such as those made by Shionogi in size 00 capsules; the finished product will contain 2 mg of loperamide, 5 mg of piperine, and 150 mg of quercetin and approximately 200 mg of xylitol base per capsule.

Example 6

Preparation of Cyclosporine Oral Modified Release with Liquid $CO_2$:

A) Preparation of Cyclosporine:Xylitol Crystals
1. Weigh out 15 g of cyclosporine (API).
2. If necessary, vacuum dry the API at a temperature of 39° C. at a pressure of <50 mm Hg for 5 hours.
3. Place the API in the loading area of the extraction processing tank.
4. Add anhydrous ethanol to the API in the loading area of the extraction processing tank; 1 volume anhydrous ethanol to 3 volumes API.
5. The extraction processing tank of 1 L in volume is compressed to 170 PSI at a temperature of −50° C. with a liquid solvent consisting of 95% $CO_2$ and 5% of an 85% aqueous ethanol solution.
6. The agitator in the extraction processing tank shall be engaged at a speed of approximately 500 RPM.
7. Compress approximately 10 times the volume of the liquid carbon dioxide solvent, to that of the API through the raw API and subsequently through the filtration apparatus upon which it rests (a 0.5 μm nylon filter) at a flow rate of 20 linear inches/min.
8. Recirculate the collected solvent and dissolved raw material through extraction tank for 5 minutes.
9. Load the excipient transfer processing tank with 76.5 g of xylitol.
10. Equilibrate the excipient phase transfer processing tank, 10 liters in volume, 170 PSI at a temperature of −50° C. with a liquid $CO_2$ based solvent consisting of 95% $CO_2$ and 5% of an 85% aqueous ethanol solution.
11. Pump the API:solvent solution produced in the extraction processing tank into the excipient transfer processing tank.
12. Repeat steps (5)-(8) and (11) until the all raw material and residue thereof is fully dissolved and transferred to the excipient transfer tank.
13. Set the agitator in the excipient transfer processing tank speed to 2000 RPM and homogenize
14. Once a solution is formed and the excipient is fully dissolved, pressure is decreased at a rate of 20 PSI/min, with the temperature maintained constantly until the solvent becomes a gas and solid crystals of API:xylitol have formed.
15. The excipient transfer processing tank is then equilibrated to ±1 psi of atmospheric pressure at room temperature, as necessary, to safely open the tank and remove the crystals of API:xylitol.
16. The API:xylitol may be dried if necessary by means of vacuum drying at a temperature of 39° C. and a pressure of <50 mmHg for 5 hours before or after removal from the tank.
17. Remove the cyclosporine:xylitol crystals.
18. The spent solvent is recovered and pumped through a graphite and silica filter.
19. The apparatus as a whole (extraction processing tank, excipient transfer processing tank, and all plumbing) is repeatedly flushed with liquid carbon dioxide and/or liquid carbon dioxide until all residue from the process is removed and the apparatus is tested negative for residual cyclosporine. The solvent is continually recovered per step (18).

B) Preparation of Piperine:Xylitol Crystals
20. Weigh out 10 g of piperine (or bioperine).
21. If necessary, vacuum dry the piperine at a temperature of 39° C. at a pressure of <50 mm Hg for 5 hours.
22. Place the piperine in the loading area of the extraction processing tank.
23. Add anhydrous ethanol to the piperine in the loading area of the extraction processing tank; 1 volume anhydrous ethanol to 3 volumes piperine.
24. The extraction processing tank of 1 L in volume is compressed to 170 PSI at a temperature of −50° C. with a liquid solvent consisting of 95% $CO_2$ and 5% of an 85% aqueous ethanol solution.
25. The agitator in the extraction processing tank shall be engaged at a speed of approximately 500 RPM.
26. Compress the liquid carbon dioxide solvent, to that of the API through the raw piperine and subsequently through the filtration apparatus upon which it rests (a 0.5 μm nylon filter) at a flow rate of 20 linear inches/min.
27. Recirculate the collected solvent and dissolved raw material through extraction tank for 5 minutes.
28. Load the excipient transfer processing tank with 51 g of xylitol.
29. Equilibrate the excipient phase transfer processing tank, 10 liters in volume, 170 PSI at a temperature of −50° C. with a liquid solvent consisting of 95% $CO_2$ and 5% of an 85% aqueous ethanol solution.
30. Pump the piperine:solvent solution produced in the extraction processing tank into the excipient transfer processing tank.
31. Repeat steps (24)-(27) and (30) until the all raw material and residue thereof is fully dissolved and transferred to the excipient transfer tank.
32. Set the agitator in the excipient transfer processing tank speed to 2000 RPM and homogenize
33. Once a solution is formed and the excipient is fully dissolved, pressure is decreased at a rate of 20 PSI/min, with the temperature maintained constantly until the solvent becomes a gas and solid crystals of piperine:xylitol have formed.
34. The excipient transfer processing tank is then equilibrated to ±1 psi of atmospheric pressure at room temperature, as necessary, to safely open the tank and remove the crystals of API:xylitol.
35. The piperine:xylitol may be dried if necessary by means of vacuum drying at a temperature of 39° C. and a pressure of <50 mmHg for 5 hours before or after removal from the tank.
36. Remove the piperine:xylitol crystals.
37. The spent solvent is recovered and pumped through a graphite and silica filter.
38. The apparatus as a whole (extraction processing tank, excipient transfer processing tank, and all plumbing) is repeatedly flushed with liquid carbon dioxide and/or liquid carbon dioxide until all residue from the process is removed and the apparatus is tested negative for residual piperine. The solvent is continually recovered per step (37).

C) Preparation of Quercitin:Xylitol Crystals
39. Weigh out 75 g of quercitin.
40. If necessary, vacuum dry the quercitin at a temperature of 39° C. at a pressure of <50 mm Hg for 5 hours.

41. Place the API in the loading area of the extraction processing tank.
42. Add anhydrous ethanol to the quercitin in the loading area of the extraction processing tank; 1 volume anhydrous ethanol to 3 volumes quercitin.
43. The extraction processing tank of 1 L in volume is compressed to 170 PSI at a temperature of −50° C. with a liquid $CO_2$ based solvent consisting of 95% $CO_2$ and 5% of an 85% aqueous ethanol solution.
44. The agitator in the extraction processing tank shall be engaged at a speed of approximately 500 RPM.
45. Compress approximately 10 times the volume of the liquid carbon dioxide solvent, to that of the API through the raw quercitin and subsequently through the filtration apparatus upon which it rests (a 0.5 μm nylon filter) at a flow rate of 20 linear inches/min.
46. Recirculate the collected solvent and dissolved raw material through extraction tank for 5 minutes.
47. Load the excipient transfer processing tank with 382.5 g of xylitol.
48. Equilibrate the excipient phase transfer processing tank, 10 liters in volume, 170 PSI at a temperature of −50° C. with a liquid solvent consisting of 95% $CO_2$ and 5% of an 85% aqueous ethanol solution.
49. Pump the quercitin: solvent solution produced in the extraction processing tank into the excipient transfer processing tank.
50. Repeat steps (43)-(46) and (49) until the all raw material and residue thereof is fully dissolved and transferred to the excipient transfer tank.
51. Set the agitator in the excipient transfer processing tank speed to 2000 RPM and homogenize
52. Once a solution is formed and the excipient is fully dissolved, pressure is decreased at a rate of 20 PSI/min, with the temperature maintained constantly until the solvent becomes a gas and solid crystals of quercitin: xylitol have formed.
53. The excipient transfer processing tank is then equilibrated to ±1 psi of atmospheric pressure at room temperature, as necessary, to safely open the tank and remove the crystals of API:xylitol.
54. The quercitin: xylitol may be dried if necessary by means of vacuum drying at a temperature of 39° C. and a pressure of <50 mmHg for 5 hours before or after removal from the tank.
55. Remove the quercitin: xylitol crystals.
56. The spent solvent is recovered and pumped through a graphite and silica filter.
57. The apparatus as a whole (extraction processing tank, excipient transfer processing tank, and all plumbing) is repeatedly flushed with liquid carbon dioxide and/or liquid carbon dioxide until all residue from the process is removed and the apparatus is tested negative for residual quercitin. The solvent is continually recovered per step (56).

D) Final Processing and Encapsulation

58. Prepare the final product by blending the cyclosporine:xylitol with the piperine:xylitol and quercetin:xylitol, as well as addition of stabilizers and emollients such as vegetable oils, waxes, lecithin, fats, semi-solid and liquid polyols, and antioxidants such as tocopherols, ascorbates, thymol, etc. Anti-caking agents such as corn starch, potato starch, or magnesium stearate may also be added.
59. Encapsulate the final product using standard encapsulation equipment such as those made by Shionogi in size 00 capsules; the finished product will contain 15 mg of the drug cyclosporine, 10 mg of piperine, and 75 mg of quercetin and approximately 750 mg of xylitol base per capsule.

Example 7

Preparation of Tacrolimus Oral Modified Release with Supercritical $CO_2$:

A) Preparation of Tacrolimus:Xylitol Crystals

1. Weigh out 0.25 g of raw tacrolimus (API).
2. If necessary, vacuum dry the API at a temperature of 39° C. at a pressure of <50 mm Hg for 5 hours.
3. Place the API in the loading area of the extraction processing tank.
4. The extraction processing tank of 1 L in volume is compressed to 1200 PSI at a temperature of 35° C. with a supercritical solvent consisting of 95% $CO_2$ and 5% of an 85% aqueous ethanol solution.
5. The agitator in the extraction processing tank shall be engaged at a speed of approximately 500 RPM.
6. Compress the supercritical carbon dioxide solvent, through the filtration apparatus upon which it rests (a 0.5 μm nylon filter) at a flow rate of 20 linear inches/min.
7. Recirculate the collected solvent and dissolved raw material through extraction tank for 5 minutes;
8. Load the excipient transfer processing tank with 1.8 g of xylitol USP.
9. Equilibrate the excipient phase transfer processing tank, 10 liters in volume, 1200 PSI at a temperature of 35° C. with a supercritical solvent consisting of 95% $CO_2$ and 5% of an 85% aqueous ethanol solution.
10. Pump the API:solvent solution produced in the extraction processing tank into the excipient transfer processing tank.
11. Repeat steps (4)-(7) and (10) until the all raw material and residue thereof is fully dissolved and transferred to the excipient transfer tank.
12. Set the agitator in the excipient transfer processing tank speed to 2000 RPM and homogenize
13. Once a solution is formed and the excipient is fully dissolved, pressure is decreased at a rate of 20 PSI/min, with the temperature maintained constantly until the solvent becomes a gas and solid crystals of API:xylitol have formed.
14. The excipient transfer processing tank is then equilibrated to ±1 psi of atmospheric pressure at room temperature, as necessary, to safely open the tank and remove the crystals of API:xylitol.
15. The API:xylitol may be dried if necessary by means of vacuum drying at a temperature of 39° C. and a pressure of <50 mmHg for 5 hours before or after removal from the tank.
16. Remove the tacrolimus:xylitol crystals.
17. The spent solvent is recovered and pumped through a graphite and silica filter.
18. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual tacrolimus. The solvent is continually recovered per step (17).

B) Preparation of Piperine:Xylitol Crystals

19. Weigh out 5 g of piperine.
20. If necessary, vacuum dry the piperine at a temperature of 39° C. at a pressure of <50 mm Hg for 5 hours.

21. Place the piperine in the loading area of the extraction processing tank.
22. The extraction processing tank of 1 L in volume is compressed to 1200 PSI at a temperature of 35° C. with a supercritical solvent consisting of 95% $CO_2$ and 5% of an 85% aqueous ethanol solution.
23. The agitator in the extraction processing tank shall be engaged at a speed of approximately 500 RPM.
24. Compress the supercritical carbon dioxide solvent through the raw piperine, through the filtration apparatus upon which it rests (a 0.5 µm nylon filter) at a flow rate of 20 linear inches/min.
25. Recirculate the collected solvent and dissolved raw material through extraction tank for 5 minutes.
26. Load the excipient transfer processing tank with 21.7 g of xylitol.
27. Equilibrate the excipient phase transfer processing tank, 10 liters in volume, 1200 PSI at a temperature of 35° C. with a supercritical solvent consisting of 95% $CO_2$ and 5% of an 85% aqueous ethanol solution.
28. Pump the piperine:solvent solution produced in the extraction processing tank into the excipient transfer processing tank.
29. Repeat steps (22)-(25) and (28) until the all raw material and residue thereof is fully dissolved and transferred to the excipient transfer tank.
30. Set the agitator in the excipient transfer processing tank speed to 2000 RPM and homogenize
31. Once a solution is formed and the excipient is fully dissolved, pressure is decreased at a rate of 20 PSI/min, with the temperature maintained constantly until the solvent becomes a gas and solid crystals of piperine:xylitol have formed.
32. The excipient transfer processing tank is then equilibrated to ±1 psi of atmospheric pressure at room temperature, as necessary, to safely open the tank and remove the crystals of piperine:xylitol.
33. The piperine:xylitol may be dried if necessary by means of vacuum drying at a temperature of 39° C. and a pressure of <50 mmHg for 5 hours before or after removal from the tank.
34. Remove the piperine:xylitol crystals.
35. The spent solvent is recovered and pumped through a graphite and silica filter.
36. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual piperine. The solvent is continually recovered per step (35).

C) Preparation of Quercitin:Xylitol Crystals

37. Vacuum dry quercetin or a botanical source of quercetin at 39° C. and a pressure of <50 mmHg for 5 hours.
38. The raw quercetin is weighed to 75 g of quercetin or the equivalent of a botanical source containing 75 g of quercetin.
39. Place the quercitin in the loading area of the extraction processing tank.
40. The agitator in the extraction processing tank shall be engaged at a speed of approximately 500 RPM.
41. The extraction processing tank of 1 L in volume is compressed to 1200 PSI at a temperature of 35° C. with a supercritical solvent consisting of 95% $CO_2$ and 5% of an 85% aqueous ethanol solution.
42. Compress the supercritical carbon dioxide solvent through the raw quercitin, through the filtration apparatus upon which it rests (a 0.5 µm nylon filter) at a flow rate of 20 linear inches/min.
43. Recirculate the collected solvent and dissolved raw material through extraction tank for 5 minutes.
44. Load the excipient transfer processing tank with 325.4 g of xylitol.
45. Equilibrate the excipient phase transfer processing tank, 10 liters in volume, 1200 PSI at a temperature of 35° C. with a supercritical solvent consisting of 95% $CO_2$ and 5% of an 85% aqueous ethanol solution.
46. Pump the quercitin: solvent solution produced in the extraction processing tank into the excipient transfer processing tank.
47. Repeat steps (41)-(43) and (46) until the all raw material and residue thereof is fully dissolved and transferred to the excipient transfer tank.
48. Set the agitator in the excipient transfer processing tank speed to 2000 RPM and homogenize
49. Once a solution is formed and the excipient is fully dissolved, pressure is decreased at a rate of 20 PSI/min, with the temperature maintained constantly until the solvent becomes a gas and solid crystals of quercitin:xylitol have formed.
50. The excipient transfer processing tank is then equilibrated to ±1 psi of atmospheric pressure at room temperature, as necessary, to safely open the tank and remove the crystals of quercitin: xylitol.
51. The quercitin: xylitol may be dried if necessary by means of vacuum drying at a temperature of 39° C. and a pressure of <50 mmHg for 5 hours before or after removal from the tank.
52. Remove the quercitin: xylitol crystals.
53. The spent solvent is recovered and pumped through a graphite and silica filter.
54. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual quercitin. The solvent is continually recovered per step (53).

D) Final Processing and Encapsulation

55. Prepare the final product by blending the tacrolimus: xylitol with the piperine:xylitol and quercetin:xylitol, as well as addition of stabilizers and emollients such as vegetable oils, waxes, lecithin, fats, semi-solid and liquid polyols, and antioxidants such as tocopherols, ascorbates, thymol, etc. Anti-caking agents such as corn starch, potato starch, or magnesium stearate may also be added.
56. Encapsulate the final product using standard encapsulation equipment such as those made by Shionogi in size 0 capsules; the finished product will contain 0.25 mg of the drug tacrolimus, 5 mg of piperine, and 75 mg of quercetin and approximately 500 mg of xylitol base per capsule.

Example 8

Preparation of Talinolol Oral Modified Release with Liquid $CO_2$:

A) Preparation of Talinolol:Glycerin Slurry

1. Weigh out 15 g of raw talinolol (API).
2. If necessary, vacuum dry the API at a temperature of 39° C. at a pressure of <50 mm Hg for 5 hours.
3. Place the API in the loading area of the extraction processing tank.

4. The extraction processing tank of 1 L in volume is compressed to 170 PSI at a temperature of −50° C. with a liquid solvent consisting of 95% $CO_2$ and 5% of an 85% aqueous ethanol solution.
5. The agitator in the extraction processing tank shall be engaged at a speed of approximately 500 RPM.
6. Compress the liquid carbon dioxide solvent through the raw API and subsequently, at a solvent to API ratio of approximately 10:1, through the filtration apparatus upon which it rests (a 0.5 μm nylon filter) at a flow rate of 20 linear inches/min.
7. Recirculate the collected solvent and dissolved raw material through the extraction tank for 5 minutes; once completed this material is compressed API:solvent.
8. Load the excipient transfer processing tank with 99 g of glycerin.
9. Equilibrate the excipient phase transfer processing tank, 10 liters in volume, 170 PSI at a temperature of −50° C. with a liquid solvent consisting of 95% $CO_2$ and 5% of an 85% aqueous ethanol solution.
10. Pump the API:solvent solution produced in the extraction processing tank into the excipient transfer processing tank.
11. Repeat steps (4)-(7) and (10) until the all raw material and residue thereof is fully dissolved and transferred to the excipient transfer tank.
12. Set the agitator in the excipient transfer processing tank speed to 2000 RPM and homogenize.
13. Once a solution is formed and the excipient is fully dissolved, pressure is decreased at a rate of 20 PSI/min, with the temperature maintained constantly until the solvent becomes a gas and a slurry of API:glycerin have formed.
14. The excipient transfer processing tank is then equilibrated to ±1 psi of atmospheric pressure at room temperature, as necessary, to safely open the tank and remove the crystals slurry of API:glycerin.
15. The API:glycerin may be dried if necessary by means of vacuum drying at a temperature of 39° C. and a pressure of <50 mmHg for 5 hours before or after removal from the tank.
16. Remove the talinolol:glycerin slurry.
17. The spent solvent is recovered and pumped through a graphite and silica filter.
18. The apparatus as a whole (extraction processing tank, excipient transfer processing tank, and all plumbing) is repeatedly flushed with liquid carbon dioxide and/or supercritical carbon dioxide until all residue from the process is removed and the apparatus is tested negative for residual talinolol. The solvent is continually recovered per step (17).

B) Preparation of Piperine:Glycerin Slurry
19. Weigh out 10.0 g of piperine.
20. If necessary, vacuum dry the piperine at a temperature of 39° C. at a pressure of <50 mm Hg for 5 hours.
21. Place the piperine in the loading area of the extraction processing tank.
22. The extraction processing tank of 1 L in volume is compressed to 170 PSI at a temperature of −50° C. with a liquid solvent consisting of 98% $CO_2$ and 2% of a 99% aqueous solution of ethanol at a PH of 11.
23. The agitator in the extraction processing tank shall be engaged at a speed of approximately 500 RPM.
24. Compress the liquid carbon dioxide solvent through the raw piperine, through the filtration apparatus upon which it rests (a 0.5 μm nylon filter) at a flow rate of 20 linear inches/min.
25. Recirculate the collected solvent and dissolved raw material through extraction tank for 5 minutes.
26. Load the excipient transfer processing tank with 66.0 g of glycerin.
27. Equilibrate the excipient phase transfer processing tank, 10 liters in volume, 170 PSI at a temperature of −50° C. with a liquid solvent consisting of 98% $CO_2$ and 2% of a 99% aqueous solution of ethanol at a PH of 11.
28. Pump the piperine:solvent solution produced in the extraction processing tank into the excipient transfer processing tank.
29. Repeat steps (22)-(25) and (28) until the all raw material and residue thereof is fully dissolved and transferred to the excipient transfer tank.
30. Set the agitator in the excipient transfer processing tank speed to 2000 RPM and homogenize
31. Once a solution is formed and the excipient is fully dissolved, pressure is decreased at a rate of 20 PSI/min, with the temperature maintained constantly until the solvent becomes a gas, and slurry of piperine:glycerin have formed.
32. The excipient transfer processing tank is then equilibrated to ±1 psi of atmospheric pressure at room temperature, as necessary, to safely open the tank and remove the slurry of piperine:glycerin.
33. The piperine:glycerin may be dried if necessary by means of vacuum drying at a temperature of 39° C. and a pressure of <50 mmHg for 5 hours before or after removal from the tank.
34. Remove the piperine:glycerin slurry.
35. The spent solvent is recovered and pumped through a graphite and silica filter.
36. The apparatus as a whole (extraction processing tank, excipient transfer processing tank, and all plumbing) is repeatedly flushed with liquid carbon dioxide and/or liquid carbon dioxide until all residue from the process is removed and the apparatus is tested negative for residual piperine. The solvent is continually recovered per step (35).

C) Preparation of Quercitin:Xylitol Crystals
37. Vacuum dry quercetin or a botanical source of quercetin at 39° C. and a pressure of <50 mmHg for 5 hours.
38. The raw quercetin is weighed to 50.0 g of quercetin or the equivalent of a botanical source containing 50.0 g of quercetin.
39. Place the quercitin in the loading area of the extraction processing tank.
40. The extraction processing tank of 1 L in volume is compressed to 170 PSI at a temperature of −50° C. with a liquid $CO_2$ based solvent consisting of 95% $CO_2$ and 5% of an 85% aqueous ethanol solution.
41. The agitator in the extraction processing tank shall be engaged at a speed of approximately 500 RPM.
42. Compress the liquid carbon dioxide solvent through the raw quercitin through the filtration apparatus upon which it rests (a 0.5 μm nylon filter) at a flow rate of 20 linear inches/min.
43. Recirculate the collected solvent and dissolved raw material through extraction tank for 5 minutes; once completed this material is compressed quercitin: solvent.
44. Load the excipient transfer processing tank with 330.0 g of xylitol.
45. Equilibrate the excipient phase transfer processing tank, 10 liters in volume, 170 PSI at a temperature of −50° C. with a liquid solvent consisting of 95% $CO_2$ and 5% of an 85% aqueous ethanol solution.
46. Pump the quercitin: solvent solution produced in the extraction processing tank into the excipient transfer processing tank.
47. Repeat steps (40)-(43) and (46) until the all raw material and residue thereof is fully dissolved and transferred to the excipient transfer tank.
48. Set the agitator in the excipient transfer processing tank speed to 2000 RPM and homogenize
49. Once a solution is formed and the excipient is fully dissolved, pressure is decreased at a rate of 20 PSI/min, with the temperature maintained constantly until the solvent becomes a gas and solid crystals of quercitin: xylitol have formed.
50. The excipient transfer processing tank is then equilibrated to ±1 psi of atmospheric pressure at room temperature, as necessary, to safely open the tank and remove the crystals of quercitin: xylitol.
51. The quercitin: xylitol may be dried if necessary by means of vacuum drying at a temperature of 39° C. and a pressure of <50 mmHg for 5 hours before or after removal from the tank.
52. Remove the quercitin: xylitol crystals.
53. The spent solvent is recovered and pumped through a graphite and silica filter.
54. The apparatus as a whole (extraction processing tank, excipient transfer processing tank, and all plumbing) is repeatedly flushed with liquid carbon dioxide and/or liquid carbon dioxide until all residue from the process is removed and the apparatus is tested negative for residual quercitin. The solvent is continually recovered per step (53).

D) Final Processing and Encapsulation

55. Prepare the final product by blending the talinolol: glycerin with the piperine:glycerin and quercetin:xylitol, as well as addition of stabilizers and emollients such as vegetable oils, waxes, lecithin, fats, semi-solid and liquid polyols, and antioxidants such as tocopherols, ascorbates, thymol, etc. Anti-caking agents such as corn starch, potato starch, or magnesium stearate may also be added.
56. Encapsulate the final product using standard encapsulation equipment such as those made by Shionogi in size 0 capsules; the finished product will contain 15 mg of the drug talinolol, 10 mg of piperine, and 50 mg of quercetin and approximately 500 mg of glycerin base per capsule.

The foregoing is illustrative of the present invention, is not to be construed as limited to the specific embodiments disclosed, and that modifications to the disclosed embodiments, as well as other embodiments, are intended to be included within the scope of the appended claims. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

I claim:

1. A process for providing an oral pharmaceutical formulation for a low solubility, low permeability and/or p-glycoprotein efflux transporter substrate active pharmaceutical ingredient or herbal extract by complexing said a low solubility, low permeability and/or p-glycoprotein efflux transporter substrate active pharmaceutical ingredient or herbal extract with a carbohydrate using a supercritical fluid, the process comprising the steps of:
   a. placing the active pharmaceutical ingredient or herbal extract in an extraction processing tank on top of a filter apparatus;
   b. compressing said extraction processing tank to a pressure of no more than 1500 PSI a temperature of no more than 150° C. and a supercritical or liquid carbon dioxide solution;
   c. agitating said active pharmaceutical ingredient or herbal extract;
   d. compressing said carbon dioxide solution through said active pharmaceutical ingredient or herbal extract, followed by compression through a filtration apparatus at a flow rate of no more than 100 linear inches/min;
   e. loading an API:solvent to API:excipient processing tank processing tank with a carbohydrate excipient;
   f. equilibrating said API:solvent to API:excipient processing tank processing tank to a pressure of no more than 1500 PSI a temperature of no more than 42° C. and a supercritical carbon dioxide solution;
   g. pumping the active pharmaceutical ingredient or herbal extract and solvent into said excipient transfer processing tank;
   h. reducing the pressure in said excipient processing tank; wherein said API and carbohydrate fall out of solution and form an API:carbohydrate complex;
   i. removing spent carbon dioxide solvent, compressing said spent carbon dioxide solvent through a filter, re-compressing said spent carbon dioxide into a holding tank;
   j. removing said API:carbohydrate complex from said extraction processing tank;
   k. placing the quercitin extract in an extraction processing tank on top of a filter apparatus;
   l. compressing said extraction processing tank to a pressure of no more than 1500 PSI a temperature of no more than 42° C. and a supercritical or liquid carbon dioxide solution;
   m. agitating said active pharmaceutical ingredient or herbal extract;
   n. compressing said carbon dioxide solution through said active pharmaceutical ingredient or herbal extract, followed by compression through a filtration apparatus at a flow rate of no more than 100 linear inches/min;
   o. loading an quercitin:solvent to quercitin:excipient processing tank processing tank with a carbohydrate excipient;
   p. equilibrating said quercitin:solvent to quercitin:excipient processing tank processing tank to a pressure of no more than 1500 PSI a temperature of no more than 42° C. and a supercritical carbon dioxide solution;
   q. pumping the active pharmaceutical ingredient or herbal extract and solvent into said excipient transfer processing tank;
   r. reducing the pressure in said excipient processing tank; wherein said quercitin and carbohydrate fall out of solution and form an quercitin:carbohydrate complex;
   s. removing spent carbon dioxide solvent, compressing said spent carbon dioxide solvent through a filter, re-compressing said spent carbon dioxide into a holding tank;
   t. removing said quercitin:carbohydrate complex from said extraction processing tank;

u. placing the piperine extract in an extraction processing tank on top of a filter apparatus;
v. compressing said extraction processing tank to a pressure of no more than 1500 PSI a temperature of no more than 42° C. and a supercritical or liquid carbon dioxide solution;
w. agitating said active pharmaceutical ingredient or herbal extract;
x. compressing said carbon dioxide solution through said active pharmaceutical ingredient or herbal extract, followed by compression through a filtration apparatus at a flow rate of no more than 100 linear inches/min;
y. loading an piperine:solvent to piperine:excipient processing tank processing tank with a carbohydrate excipient;
z. equilibrating said piperine:solvent to piperine:excipient processing tank processing tank to a pressure of no more than 1500 PSI a temperature of no more than 42° C. and a supercritical carbon dioxide solution;
aa. pumping the active pharmaceutical ingredient or herbal extract and solvent into said excipient transfer processing tank;
bb. reducing the pressure in said excipient processing tank; wherein said piperine and carbohydrate fall out of solution and form an piperine:carbohydrate complex;
cc. removing spent carbon dioxide solvent, compressing said spent carbon dioxide solvent through a filter, re-compressing said spent carbon dioxide into a holding tank;
dd. removing said piperine:carbohydrate complex from said extraction processing tank;
ee. blending said API:carbohydrate, said piperine:carbohydrate and said quercitin carbohydrate to the desired concentration.

2. The process of claim 1, wherein the API or herbal extract is a biopharmaceutical classification system class III, low permeability, high solubility material, or a class IV low permeability, high solubility material, and a p-glycoprotein substrate.

3. The process of claim 1, wherein the API or herbal extract is a biopharmaceutical classification system class III, low permeability, high solubility material, or a class IV low permeability, high solubility material, and not be a p-glycoprotein substrate.

4. The process of claim 1, wherein the said carbohydrate excipient is monosaccharide, disaccharide, oligosaccharide or alcohol sugar of no more than 21 units, is selected among a group of glycerin, xylitol, mannitol, erythritol, sorbitol, sucrose, dextrose, its counter enantiomer, fructose, lactose, galactose, ribose, deoxyribose, potato starch and corn starch.

* * * * *